United States Patent [19]

Yokoyama et al.

[11] 4,118,388

[45] Oct. 3, 1978

[54] PROCESS FOR PRODUCING PYRIDINE

[75] Inventors: Takushi Yokoyama; Hidetaka Kojima; Masaharu Uragami; Kathuyoshi Miwa, all of Ooi, Japan

[73] Assignee: Daicel, Ltd., Sakai, Japan

[21] Appl. No.: 823,477

[22] Filed: Aug. 10, 1977

[30] Foreign Application Priority Data

Aug. 11, 1976 [JP] Japan .................................. 51/96249

[51] Int. Cl.$^2$ .......................................... C07D 213/16
[52] U.S. Cl. .................................. 260/290 R; 252/467
[58] Field of Search ..................................... 260/290 R

[56] References Cited

U.S. PATENT DOCUMENTS

| | | | |
|---|---|---|---|
| 2,504,172 | 4/1950 | Arnold | 260/290 R |
| 3,334,101 | 8/1967 | Myerly et al. | 260/290 R |
| 3,335,144 | 8/1967 | Cislak et al. | 260/290 R |

FOREIGN PATENT DOCUMENTS

| | | | |
|---|---|---|---|
| 1,152,878 | 5/1969 | United Kingdom | 260/290 R |
| 1,191,913 | 5/1970 | United Kingdom | 260/290 R |

*Primary Examiner*—Alan L. Rotman

*Attorney, Agent, or Firm*—Sughrue, Rothwell, Mion, Zinn and Macpeak

[57] ABSTRACT

A process for producing pyridine which comprises oxidatively dealkylating an alkylpyridine, an alkenylpyridine or a mixture thereof in the gaseous phase with molecular oxygen and steam in the presence of a catalyst comprising active components with a general composition of the formula

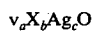

$$V_a X_b Ag_c O$$

wherein $a$, $c$, and $d$ respectively represent the atomic proportions of vanadium, silver and oxygen; X represents at least one element selected from the group consisting of chromium, molybdenum and tungsten; $b$ represents the atomic proportion of X; and when $a$ is 1, $b$ is about 0.1 to about 1.5, $c$ is about 0.005 to about 1.0, and $d$ represents the atomic proportion of oxygen, is a value determined by the atomic valences of the individual V, X and Ag elements and is about 2.6 to about 7.5; and separating pyridine from the reaction product.

10 Claims, No Drawings

PROCESS FOR PRODUCING PYRIDINE

BACKGROUND OF THE INVENTION

1. Field of the Invention

This invention relates to a process for producing pryidine by the oxidative dealkylation of alkylpyridines or alkenylpyridines.

2. Description of the Prior Art

Various synthetic methods have been developed for producing pyridine bases, and the production of pyridine bases has already been performed commercially. Current commercial methods for producing pyridine bases, however, yield fairly large amounts of akylpyridines in addition to pyridine. The consumption of pyridine as a raw material for agricultural chemicals, etc. has recently increased, and an imbalance has arisen in the supply and demand between pyridine and alkylpyridines. Hence, attention has been diverted to methods for producing pyridine which do not involve the formation of alkylpyridines, and further to methods for producing pyridine by affirmatively dealkylating alkylpyridines.

The production of pyridine by dealkylation of alkylpyridines is known (e.g., as described in U.S. Pat. Nos. 2,504,172, 3,335,144 and 3,334,101), and various processes have been investigated. Most of these dealkylating methods are hydrogenating dealkylation methods using hydrogen. However, since hydrogenating dealkylation requires a reaction apparatus capable of withstanding pressure, an oxidative dealkylation which can be performed in a reaction apparatus at normal atomspheric pressure is simpler in terms of the reaction equipment involved. However, only a few prior art techniques involving an oxidative dealkylation in the presence of a gas containing oxygen are known (e.g., as described in *Latv. PSR Zinat. Akad. Vestis, Khim. Ser.* (5) P559 (1969), *Vopr. Khim, Khim. Tekhnol.* vol 30, P140 (1974) and *J. Appl. Chem. Bietechnol* vol 26, P375 (1976)).

The method disclosed in British Pat. No. 1,191,913, which also is a prior art method for dealkylating alkylpyridines in the presence of an oxygen-containing gas, is characterized by using a vanadium-chromium type catalyst (optionally containing Cd, Bi, Ni, or Co as a promotor). When in this method, α-picoline, steam and air are used in a molar ratio of 1:20:15, the conversion of α-picoline is 94%, and the yield of pyridine is 63.7%. However, when the α-picoline is replaced by β-picoline, the conversion of the β-picoline is 75%, and the yield of pyridine is as low as 40.6%. Likewise, with γ-picoline, the conversion is 87% and the yield is 56.8%. None of these results are satisfactory.

British Pat. No. 1,152,878, on the other hand, discloses a binary-element catalyst composed of an oxide of Cr, Co or Ag and $V_2O_5$ supported on alumina as a catalyst for producing cyanopyridine by ammonxidation of alkylpyridines. The disclosure further is that by selecting the reaction conditions in the ammonxidation of an alkylpyridine with a V-Cr type catalyst, pyridine is obtained from α-picoline at a selectivity of 66.5%. However the method disclosed in British Pat. No. 1,152,878 is not satisfactory as a process for producing pyridine by dealkylation because ammonia is used in the reaction, cyanopyridine is formed simultaneously, and the reaction results are not satisfactory. In addition, no specific technical disclosure with respect to alkylpyridines other than α-picoline is given in this patent.

SUMMARY OF THE INVENTION

After extensive investigations on catalyst activities in order to remedy the defects of known prior art methods and to produce pyridine in high yields, it has now been found that the single-pass yield of pyridine can be markedly increased by using a novel catalyst of the composition described below, which mainly contains silver.

Accordingly the present invention provides a process for producing pyridine in a high yield, the method comprising oxidatively dealkylating an alkylpyridine, an alkenylpyridine or a mixture thereof in the gaseous phase with steam and molecular oxygen in the presence of a catalyst having the general composition $$V_aX_bAg_cO_d$$

wherein $a$, $c$ and $d$ respectively represent the atomic proportions of vanadium, silver and oxygen; X represents at least one element selected from the group consisting of chromium, molybdenum and tungsten; $b$ represents the atomic proportion of X; and when $a$ is 1, $b$ is about 0.1 to about 1.5, $c$ is about 0.005 to about 1.0, and $d$ represents the atomic proportion of oxygen, is a value determined by the atomic valences of the individual elements and is usually about 2.6 to about 7.5.

DETAILED DESCRIPTION OF THE INVENTION

Suitable alkylpyridines or alkenylpyridines which can be used as starting materials in the present invention are those having at least one alkyl or alkenyl group which can be straight chain or branched chain and which can contain 1 to 7 carbon atoms on the pyridine nucleus e.g., having the general formula

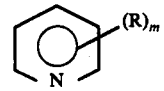

wherein R represents an alkyl group having 1 to 7 carbon atoms or an alkenyl group having 1 to 7 carbon atoms, and m represents 1 to 5. Suitable specific examples include alkylpyridines e.g., picolines

[i.e. methylpyridine ( 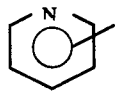 )] such as

α-picoline ( 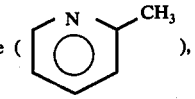 ),

β-picoline ( 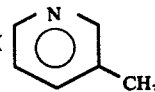 ), or

γ-picoline ( 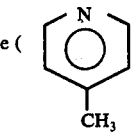 ), lutidines [i.e., dimethylpyridine ( 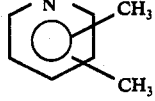 ) or

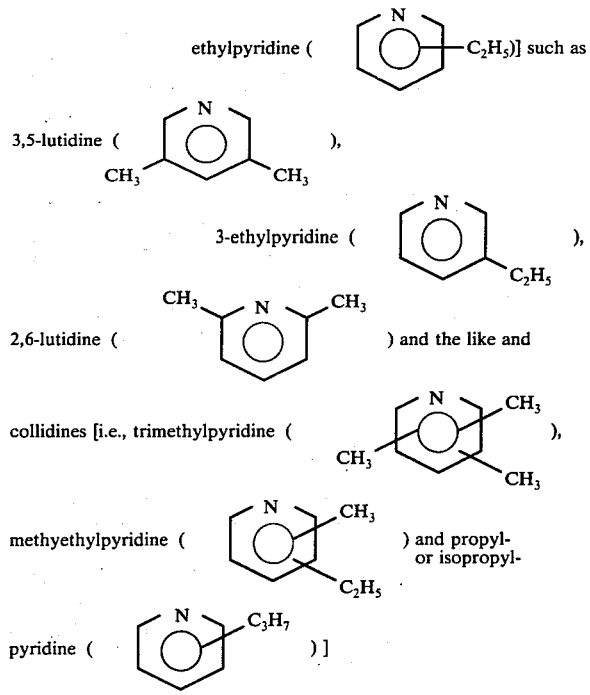

such as, 2-methyl-5-ethylpyridine, 2-propylpyridine, 2-isopropylpyridine, 2,3,5-trimethylpyridine and the like, long-chain alkyl-substituted pyridines, e.g., having 4 to 7 carbon atoms in the long-chain alkyl moiety, such as butylpyridine, pentylpyridine, hexylpyridine, heptyl-pyridine, etc. and alkenylpyridines, e.g., vinylpyridines such as 2-vinylpyridine and 2-methyl-5-vinylpyridine and mixtures of these compounds. One example of an alkylpyridine mixture is an alkylpyridine mixture obtained by removing pyridine and a tar component from the product of pyridine synthesis between an aldehyde or aldehydes such as acrolein, formaldehyde, acetaldehyde, propionaldehyde or crotonaldehyde and ammonia. For simplicity in the description to be given hereinafter, the term "alkylpyridine" will be used to describe alkylpyridines, alkenylpyridines and mixtures thereof.

The source of the molecular oxygen employed in the process of this invention may be pure oxygen or an oxygen-containing gas such as air enriched with oxygen, or air itself. For economic reasons, it is desirable to use air as the source of the molecular oxygen. Other oxygen-containing gases which can be used include mixtures of oxygen and an inert gas such as nitrogen, argon, and carbon dioxide, etc. A suitable minimum oxygen concentration which can be employed when an oxygen-containing gas is used is about 5 volume %.

Steam which is to be fed into the reaction system together with the alkylpyridine and the oxygen-containing gas serves to prevent explosions and assure safety as well as to increase the yield of pyridine. If further required from a safety viewpoint, an inert gas such as nitrogen or argon may be used as a diluent.

Examples of suitable catalyst-forming materials include vanadium compounds such as ammonium metavanadate, vanadyl chloride, meta- or pyro-vanadic acid, vanadium oxalate and vanadium oxide, chromium compounds such as the nitrates, hydrochlorides or oxides of chromium or chromic acid, molybdenum compounds such as molybdic acid, ammonium molybdate or molybdenum oxide, tungsten compounds such as tungstic acid, ammonium tungstate or tungsten oxide, and silver compounds such as silver oxide, silver nitrate and silver salts of organic acids such as silver acetate or silver lactate. Preferred examples of catalyst-forming materials include ammonium metavanadate, chromium nitrate and silver nitrate.

The catalyst used in accordance with this invention can be used either unsupported or supported on a suitable carrier. When an unsupported catalyst is desired, a uniform solution containing the above described catalyst-forming materials is solidified. After drying, the solid is calcined in an oxidative atomosphere, e.g., in air, at high temperature (e.g., about 450° C. to about 600° C.). The calcined solid is powdered to obtain a powdered catalyst which can be used as a fluidized bed catalyst or the calcined solid is molded to obtain a tableted catalyst which can be used as a fixed bed catalyst. The catalyst is more effective when it is used supported on a carrier. Suitable carriers which can be used when the catalyst is supported are, for example, alumina, silica, silicon carbide, and pumice. The amount of the carrier will vary depending on the type of the carrier, but desirably the amount of the carrier is generally not more than about 95% by weight, particularly 5 to 95% by weight.

The catalyst employed in the invention can be prepared using methods generally utilized in the preparation of catalysts of this kind. For example, oxalic acid can be gradually added to a heated aqueous suspension of ammonium metavanadate to form a uniform solution. Furthermore, chromium nitrate and silver nitrate are then added to the solution and a uniform solution obtained. The solution is sprayed onto a heated carrier to impregnate the carrier with the thus-prepared solution. After complete impregnation, the carrier is dried, and calcined in an oxidative atmosphere, e.g., in air, at high temperatures (e.g., about 450° C. to 600° C., preferably about 540° C.) to form a catalyst. Alternatively, the carrier may be used in the form of a powder and a catalyst may be finally obtained by molding the material using a tableting machine.

The catalyst used in accordance with this invention can be employed either as a fluidized bed catalyst or as a fixed bed catalyst. There is no particular restriction on the size of the catalyst particles. The particle size may be determined optionally depending on whether the catalyst is used as a fluidized bed catalyst or as a fixed bed catalyst. A suitable catalyst particle size ranges from about 30 to about 60 microns for a fluidized bed catalyst and when the catalyst is used as a fixed bed catalyst a suitable form is a cylindrical, spherical or globular form having a size ranging from about 3mmφ to about 8mmφ.

The metal atomic ratio of the active components of the catalyst used in this invention is such that, per atom of vanadium, the catalyst contains about 0.005 to about 1 atom, preferably 0.02 to 0.5 atom, of silver, and about 0.1 to about 1.5 atoms, preferably 0.2 to 1 atom, of at least one element selected from the group consisting of chromium, molybdenum and tungsten. The atomic ratio of the metal atoms to the oxygen atom is determined by the atomic valences of the individual elements.

By using the silver-containing catalyst having the metal atomic proportions or ratios specified above in the oxidative dealkylation of an alkylpyridine using a known gas-solid catalytic reaction method, good results, which cannot be anticipated from the prior art, can be obtained with regard to the conversion of the alkylpyridine and the yield of pyridine.

The oxidative dealkylation reaction in this invention can be performed without any particular restrictions on pressure. Suitable exemplary pressures which can be used range from about 200mm Hg to a pressure of about 10 atmospheres. In the most common embodiment, the pressure of the reaction gas flowing through a fixed catalyst bed is approximately atmospheric pressure at the outlet of the reaction zone.

A suitable reaction temperature for the production of pyridine in this invention is about 300° to about 500° C., preferably about 320° to 430° C. The proportion of oxygen fed to the reaction system is suitably about 1 to 5 molecules, especially 2 to 3.5 molecules, per alkyl group present as a substituent on the alkylpyridine.

There is no particular restriction on the proportion of steam. If the proportion of steam is too small, the reaction results will be lowered, and if the proportion of steam is too large, the space-time-yield and the pyridine concentration in the reaction mixture will be reduced. Accordingly, the amount of steam is preferably 10 to 40 moles, especially 15 to 25 moles, per mole of the alkylpyridine.

A suitable contact time of the starting gas is about 0.5 to about 20 seconds, preferably 5 to 15 seconds. The contact time is represented as a calculated value from the volume velocity of gas fed and the observed volume of the catalyst under normal temperature and pressure (0° C. and 1 atm.).

As stated hereinabove, when the catalyst in accordance with this invention is used in the oxidative dealkylation process for producing an alkylpyridine, the conversion of the alkylpyridine is high, and the amounts of carbon dioxide and carbon monoxide, which are combustion products that always pose a problem when an oxidation is employed, are small. Hence, pyridine as a final product can be produced in a high single-pass yield.

Pure pyridine can be obtained form the pyridine-containing reaction mixture formed by the dealkylation reaction, by any known method such as condensation, liquid separation, extraction or distillation.

Conventional dealkylations of an alkylpyridine are directed mainly to α-picoline, and the production of pyridine from β-picoline is given only a low rating because of the disadvantage of low yields. According to the process of this invention, a very high pyridine yield can be obtained even from β-picoline under the reaction conditions in which the conversion of β-picoline is substantially 100%. This is an important advantage of the present invention in commercial practice. Frequently, β-picoline and γ-picoline are formed simultaneously, and, because they have close boiling points to each other, they are not easy to separate from each other. Since the use of a mixture of these in the process of the invention gives reaction results which are better than the sum of the results expected from using them individually, the process of the invention is very suitable for using them in a readily available mixed form.

It has now been confirmed that the catalyst used in accordance with this invention has a sufficiently long lifetime, and no change in catalyst composition is observed using atomic absorption analysis, etc., between the catalysts before and after the reaction.

The following Examples are given to illustrate the present invention in more detail. It should be noted that these Examples are not in any way to be construed as limiting the scope of the invention. Unless otherwise indicated all parts, percents, ratios and the like are by weight.

The conversion of the alkylpyridine and the single-pass yield of pyridine based on an alkylpyridine, as used in the present application, are defined by the following relationships.

$$\text{Conversion of Alkylpyridine (\%)} = \frac{(\text{Moles of Alkylpyridine Fed}) - (\text{Moles of Unreacted Alkylpyridine})}{(\text{Moles of Alkylpyridine Fed})} \times 100$$

$$\text{Single-Pass Yield of Pyridine (\%)} = \frac{(\text{Moles of Pyridine Formed})}{(\text{Moles of Alkylpyridine Fed})} \times 100$$

When a mixed alkylpyridine containing substances other than picoline is used (Examples 16, 17, 19 to 21, and 26, and Comparative Example 2), the single-pass yield is expressed as the percentage of the weight of pyridine (and β-picoline) obtained based on the weight of the alkylpyridine fed. Since the reaction in accordance with the present invention involves a reduction in molecular weight, the single-pass yield on a molar basis naturally becomes larger than the yield expressed on a weight basis.

When a mixed alkylpyridine is used, the amounts of steam and air fed are represented in terms of gram molecules per 93 g of alkylpyridine.

EXAMPLE 1

Water (100 ml) was added to 6.43 g of ammonium metavanadate, and with vigorous stirring, 5.4 g of oxalic acid was gradually added to dissolve the ammonium metavanadate completely.

Then, 20 ml of water was added to 15.66 g of chromium nitrate to dissolve the chromium nitrate completely, and then the resulting aqueous solution was added to the oxalic acid solution of ammonium metavanadate prepared as described above. Furthermore, 1.47 g of silver nitrate was completely dissolved in 20 ml of water, and the solution was added to the mixed solution obtained. The mixture was sufficiently stirred.

Separately, spherical alumina with a particle diameter of 5 mm as a carrier was heated on a sand bath, and impregnated with the mixed solution of catalyst ingredients by spraying the carrier little by little. This procedure was repeated until the mixed solution of the catalyst components was used up. Then, the resulting impregnated carrier was dried at 120° C. for 1 hour, and calcined in the air at 450° C. for 3 hours to produce the catalyst.

The resulting catalyst had the composition: $V_1Cr_{0.7}Ag_{0.16}O_{3.63}$(15% by weight) on $Al_2O_3$(85% by weight).

The catalyst (60 ml) was packed into a stainless steel U-shaped reaction tube with an inside diameter of 27.2 mm, and a gaseous mixture of β-picoline, steam and air in a molar ratio of 1:22:12 was passed through the reaction tube and reacted at 350° C. for a contact time of 8 seconds (N.T.P.). The conversion of β-picoline was 100%, and the yield of pyridine was 77%.

COMPARATIVE EXAMPLE 1

A catalyst was prepared in accordance with the method described in Example 1 above except that silver nitrate was not added. The reaction was performed under the same conditions as in Example 1. The conversion of β-picoline was 78.5%, and the yield of pyridine was 32.9%.

EXAMPLES 2 TO 10

In accordance with the method described in Example 1 above, catalysts as shown in Table 1 below were prepared. Using each of these catalysts, β-picoline was oxidatively dealkylated under the same feeding conditions at each of the temperatures shown in Table 1 below. The results obtained are shown in Table 1 below.

Table 1

| Ex. | Catalyst Composition (atomic ratio) | | | | | Reaction Temperature (° C) | Conversion of β Picoline (%) | Yield of Pyridine (%) |
| --- | --- | --- | --- | --- | --- | --- | --- | --- |
| | V: | Ag: | Cr | Mo | W | | | |
| 2 | 1 | 0.02 | 0.7 | — | — | 365 | 97.5 | 67.7 |
| 3 | 1 | 0.08 | 0.7 | — | — | 370 | 99.5 | 76.0 |
| 4 | 1 | 0.32 | 0.7 | — | — | 350 | 98.9 | 72.9 |
| 5 | 1 | 0.64 | 0.7 | — | — | 360 | 87.2 | 60.4 |
| 6 | 1 | 0.16 | 0.96 | — | — | 360 | 98.9 | 75.3 |
| 7 | 1 | 0.16 | 0.36 | — | — | 360 | 98.9 | 75.3 |
| 8 | 1 | 0.16 | — | 0.37 | — | 360 | 87.1 | 67.1 |
| 9 | 1 | 0.16 | — | — | 0.23 | 360 | 94.0 | 69.4 |
| 10 | 1 | 0.16 | 0.7 | — | — | 430 | 94.5 | 62.8 |
| 11 | 1 | 0.16 | 0.7 | — | — | 320 | 98.8 | 70.2 |

EXAMPLES 12 TO 15

Various alkylpyridines were used under the reaction conditions shown in Table 2 below using the same catalyst as in Example 1. The results obtained are shown in Table 2 below.

Table 2

| Example | Starting Material | Molar Ratio of Feed | | | Reaction Temperature (° C) | Conversion of Alkylpyridine (%) | Yeild of Pyridine (%) |
| --- | --- | --- | --- | --- | --- | --- | --- |
| | | Alkylpyridine | :H₂O : | Air | | | |
| 12 | α-Picoline | 1 | 22 | 12 | 330 | 100 | 83.2 |
| 13 | γ-Picoline | 1 | 23 | 15 | 420 | 91.4 | 67.9 |
| 14 | 2,6-Lutidine | 1 | 22 | 20 | 365 | 93.4 | 44.2 |
| 15 | 5-Ethyl-2-methylpyridine | 1 | 37 | 31 | 370 | 100 | 46.2 |

EXAMPLES 16 AND 17 AND COMPARATIVE EXAMPLE 2

Using the same catalyst as in Example 1, alkylpyridines having high-boiling components were oxidatively dealkylated. The results obtained are shown in Table 3 below.

Table 3

| Example | Starting Material | Molar Ratio of Feed | | Reaction Temperature (° C) | Yield of Pyridine (wt.%) | Yield of β-Picoline (wt.%) |
| --- | --- | --- | --- | --- | --- | --- |
| | | H₂O | Air | | | |
| 16 | β-Picoline 50.0% α-Picoline 0.3% 3,5-Lutidine 31.6% 3-Ethylpyridine 5.8% Others 12.3% | 30 | 25 | 360 | 54.9 | 16.9 |
| 17 | β-Picoline 19.7% 2,5-Lutidine 3.5% 3-Ethylpyridine 15.2% 3,5-Lutidine 40.1% Others 21.5% | 21 | 20 | 345 | 25.7 | 7.6 |
| Comparative Example 2 | Same as in Example 16 | 0 | 10 | 370 | 5 | 63 |

EXAMPLE 18

Water (40 ml) was added to 5.14 g of ammonium metavanadate, and with vigorous stirring, 8 g of oxalic acid was gradually added to dissolve the ammonium metavanadate completely. Then, 12.53 g of chromium nitrate was added to the oxalic acid solution of ammonium metavanadate prepared. Separately, 1.17 g of silver nitrate was dissolved in 10 ml of water, and after complete dissolution, the resulting solution was added to the mixed solution obtained. The mixture was sufficiently stirred to form a mixed solution of catalyst components.

Separately, 50 g of tableted γ-alumina (3 mm in diameter and 3 mm in length) as a carrier was dipped in the catalyst component solution to impregnate the carrier with the solution. The residue was separated by filtration. The γ-alumina containing the catalyst solution was coated with a spray of the above catalyst solution little by little while it was heated over a sand bath. This operation was repeated until the catalyst solution was used up. The coated product was dried at 120° C. for 1 hour, and finally calcined in air at 450° C. for 3 hours.

The resulting catalyst (60 ml) was packed into the reaction tube as described in Example 1, and a gaseous mixture of β-picoline, steam and air in a molar ratio of 1:16:12 was reacted over the catalyst at 345° C. with a contact time of 6.5 seconds (N.T.P.). The conversion of β-picoline was 97.2%, and the yield of pyridine was 84.2%.

EXAMPLES 19 TO 21

A mixed alkylpyridine containing 86.9% of β-picoline, 6.3% of 3,5-lutidine and 3-ethylpyridine taken together, and 1.6% of a α-picoline was oxidatively dealkylated at 360° C. The composition of the starting gaseous mixture and the yield of pyridine are shown in Table 4 below.

Table 4

| Example | Molar Ratio of Feed | | Yield of Pyridine (wt. %) |
| --- | --- | --- | --- |
| | H₂O | Air | |
| 19 | 23 | 11 | 62.4 |
| 20 | 10 | 11 | 49.2 |
| 21 | 5 | 11 | 40.0 |

EXAMPLES 22 TO 24

Using a catalyst having the composition as described in Example 1, β-picoline, γ-picoline, and a mixture thereof were each oxidatively dealkylated. The results obtained are shown in Table 5 below. It is seen that in the case γ-picoline, the yield of pyridine is lower than the yield in the case of β-picoline, but when a mixture of β- and γ-picolines is used, the yield of pyridine is higher than the yield in the case of using β-picoline alone.

Table 5

| Example | Picoline | Reaction Temperature (°C) | Conversion of Picoline (%) | Yield of Pyridine (%) |
|---|---|---|---|---|
| 22 | γ-picoline | 360 | 95.6 | 60.4 |
| 23 | β-picoline | 340 | 92.1 | 75.7 |
| 24 | β-picoline (90%) and γ-picoline (10%) | 340 | 95.6 | 82.6 |

EXAMPLES 25 AND 26

Using a catalyst prepared by a method similar to that in Example 18, a catalyst activity test was carried out for a long period of time at 340° C. In Example 25, β-picoline was used as a starting material, and in Example 26 a by-product alkylpyridine mixture containing 69% of β-picoline, 11.8 1 % of 3-ethylpyridine and 3,5-lutidine taken together, and the remainder collidine was used as a starting material. In Example 26, the yield was the percentage of the pyridine obtained based on the weight of the starting material charged. The results obtained are shown in Table 6 below.

Table 6

| Example 25 (β-picoline) | | Example 26 (mixture) | |
|---|---|---|---|
| Reaction Time (hours) | Conversion (%) | Yield of Pyridine (%) | Reaction Time (hours) | Yield of Pyridine (wt. %) |
| 20 | 97.5 | 76.3 | 300 | 57.0 |
| 478 | 97.1 | 77.1 | 623 | 56.4 |
| 1100 | 99.0 | 77.8 | 940 | 54.2 |
| | | | 1200 | 54.2 |
| | | | 2188 | 54.4 |

While the invention has been described in detail and with reference to specific embodiments thereof, it will be apparent to one skilled in the art that various changes and modifications can be made therein without departing from the spirit and scope thereof.

What is claimed is:

1. A process for producing pyridine which comprises oxidatively dealkylating an alkylpyridine, an alkenylpyridine, the alkyl or alkenyl groups of which have one to seven carbon atoms, or a mixture thereof in the gaseous phase with molecular oxygen and steam in the presence of a catalyst comprising active components with a general composition of the formula $$V_a X_b Ag_c O_d$$

wherein $a$, $c$ and $d$ respectively represent the atomic proportions of vanadium, silver and oxygen; X represents at least one element selected from the group consisting of chromium, molybdenum and tungsten; $b$ represents the atomic proportion of X; and when $a$ is 1, $b$ is about 0.1 to about 1.5, $c$ is about 0.005 to about 1.0, and $d$ represents the atomic proportion of oxygen, is a value determined by the atomic valences of the individual V, X and Ag elements and is about 2.6 to about 7.5; and separating pyridine from the reaction product.

2. The process of claim 1, wherein the composition of the active components is $V_1 X_{0.2-1} Ag_{0.02-0.5} O_d$.

3. The process of claim 1, wherein X is chromium.

4. The process of claim 1, wherein said alkylpyridine, alkenylpyridine or mixture thereof is β-picoline, γ-picoline or a mixture of β-picoline and γ-picoline.

5. The process of claim 1, wherein said alkylpyridine alkenylpyridine or mixture thereof is an alkylpyridine mixture obtained by removing pyridine and a tar component from the product of the synthesis of pyridine from an aldehyde or aldehydes and ammonia.

6. The process of claim 1, wherein the amount of steam is about 10 to about 40 moles per mole of said alkylpyridine, alkenylpyridine or mixture thereof.

7. The process of claim 1, wherein said alkylpyridine, alkenylpyridine or mixture thereof is α-picoline.

8. The process of claim 1, wherein the proportion of oxygen fed to the reaction system is about 1 to 5 molecules per alkyl group or alkenyl group present on the alkylpyridine or alkenylpyridine.

9. The process of claim 1, wherein the gaseous phase oxidative dealkylating is at about 300° to about 500° C.

10. The process of claim 9, wherein the gaseous phase oxidative dealkylating is at about 320° to about 430° C.

* * * * *